US012637545B2

(12) United States Patent
Garcia Mazas et al.

(10) Patent No.: US 12,637,545 B2
(45) Date of Patent: May 26, 2026

(54) POLYMERS FOR GENE THERAPY

(71) Applicant: UNIVERSIDADE DE SANTIAGO DE COMPOSTELA, Santiago de Compostela (ES)

(72) Inventors: Carla Maria Garcia Mazas, Santiago de Compostela (ES); Noemi Csaba, Santiago de Compostela (ES); Marcos Garcia Fuertes, Santiago de Compostela (ES)

(73) Assignee: UNIVERSIDADE DE SANTIAGO DE COMPOSTELA, Santiago de Compostela (ES)

( * ) Notice: Subject to any disclaimer, the term of this patent is extended or adjusted under 35 U.S.C. 154(b) by 445 days.

(21) Appl. No.: 18/250,691

(22) PCT Filed: Oct. 22, 2021

(86) PCT No.: PCT/ES2021/070771
§ 371 (c)(1),
(2) Date: Apr. 26, 2023

(87) PCT Pub. No.: WO2022/090598
PCT Pub. Date: May 5, 2022

(65) Prior Publication Data

US 2023/0383064 A1 Nov. 30, 2023

(30) Foreign Application Priority Data

Oct. 27, 2020 (ES) ................................ ES202031074

(51) Int. Cl.
*C08G 79/025* (2016.01)
*A61K 48/00* (2006.01)
*A61P 35/00* (2006.01)

(52) U.S. Cl.
CPC ........ *C08G 79/025* (2013.01); *A61K 48/0066* (2013.01); *A61P 35/00* (2018.01)

(58) Field of Classification Search
None
See application file for complete search history.

(56) References Cited

U.S. PATENT DOCUMENTS

2015/0141540 A1 * 5/2015 Golding ............... C08G 79/025 422/127
2017/0037193 A1 * 2/2017 Sohn .................... A61K 31/337

FOREIGN PATENT DOCUMENTS

KR 101892955 B1 8/2018
WO WO2017191345 11/2017

OTHER PUBLICATIONS

De Wolf et al. In vivo tumor transfection mediated by polyplexes based on biodegradable poly(DMAEA)-phosphazene, Journal of Controlled Release 2005, 109, 275-287.
Hsu et al., Polyphosphazenes for the delivery of biopharmaceuticals, J. Appl. Polym. Sci. 2020, 137(25), 48688.
Hsu et al. Structure-Optimized Interpolymer Polyphosphazene Complexes for Effective Gene Delivery against Glioblastoma, Adv. Ther. 2018, 2(3), 1800126.

* cited by examiner

*Primary Examiner* — Megan McCulley
(74) *Attorney, Agent, or Firm* — Casimir Jones, S.C.; Tristan A. Fuierer

(57) ABSTRACT

Polymers for gene therapy. The present invention relates to a polymer, more specifically a polyphosphazene polymer, that is useful for gene therapy. The invention also relates to a complex comprising the polymer, the method for producing same and uses thereof.

19 Claims, 6 Drawing Sheets

Specification includes a Sequence Listing.

POLYMERS FOR GENE THERAPY

CROSS-REFERENCE TO RELATED APPLICATIONS

This application is filed under the provisions of 35 U.S.C. § 371 and claims the priority of International Patent Application No. PCT/ES2021/070771 filed on 22 Oct. 2021 entitled "POLYMERS FOR GENE THERAPY" in the name of Carla Maria GARCIA MAZAS, et al., which claims priority to Spanish Patent Application No. P202031074, filed on 27 Oct. 2020, both of which are hereby incorporated by reference herein in their entirety.

FIELD OF THE ART

The present invention relates to a polymer, more specifically a polyphosphazene polymer, that is useful for gene therapy. The invention also relates to a complex comprising the polymer, the method for producing same and uses thereof.

BACKGROUND

In gene therapy, as well as in other biomedical areas, new biodegradable materials are required and polymers play a critical role in this field. Compared to natural polymers, synthetic biodegradable polymers are generally better defined and easier to modulate in terms of their mechanical and degradation properties. Polyesters such as polylactide (PLA), poly(lactide-co-glycolide) (PLGA) or polycaprolactone (PCL) are some of the synthetic polymers most widely used as biomaterials; however, research on other families of polymers, such as polyphosphazenes (Hsu W H, Csaba N, Alexander C, Garcia Fuentes M. *Polyphosphazenes for the delivery of biopharmaceuticals. J. Appl. Polym. Sci.* 2019, 137(25)) has begun more recently.

Polyphosphazenes are a relatively new family of nitrogen-phosphorus backbone-based polymers in which side groups can be inserted.

The first known polyphosphazene, published by Stokes in 1897, was obtained by heating (250° C.) a mixture of $PCl_5$ and $NH_4Cl$. Due to its insolubility and the lack of knowledge concerning its chemical structure, it was first called "inorganic rubber". In 1956, Allcock et. al. performed the first stable synthesis of polyphosphazenes and, from that moment on, the use of materials of this type in biomedical applications took on greater interest. The scheme developed by Allcock still serves as the basis for the most general method for the linear synthesis of polyphosphazenes: the precursor, poly(dichlorophosphazene) (PDCP), is prepared in the first step and the final polymer is then formed by means of nucleophilic substitution of the desired side chains.

Given that the synthetic route of polyphosphazenes is highly versatile, many different functionalities that completely modify the physicochemical and biological properties of polymers can be added. Polyphosphazenes can thus be designed by incorporating a series of organic side groups which make these materials biodegradable and highly biocompatible (Hsu W H, Sanchez-Gomez P, Gomez-Ibarlucea E, Ivanov D P, Rahman R, Grabowska A M, Csaba N, Alexander C, Garcia-Fuentes M. *Structure-Optimized Interpolymer polyphosphazene Complexes for Effective Gene Delivery against Glioblastoma. Adv. Ther.* 2018, 2(3)). These particularities of polyphosphazenes have stimulated growing interest, concentrated particularly in some areas such as tissue engineering, gene delivery, protein delivery, and vaccination. The biodegradability of most poly(organophosphazenes) and the chemical flexibility of these materials are particularly critical for this interest. Although other types of polymers can also be chemically diverse, the special synthesis pathway of polyphosphazenes, in which a precursor is modified to adapt the structure of the material and to meet the requirements of specific applications, is considered attractive by engineers. This synthetic route simplifies the adaptation of existing technologies to new areas of interest (Hsu W H, Csaba N, Alexander C, Garcia-Fuentes M. *Polyphosphazenes for the delivery of biopharmaceuticals. J. Appl. Polym. Sci.* 2019, 137(25)).

Nevertheless, there is still a need to provide polyphosphazene derivatives which allow an improved transfection, are biologically safe, and can furthermore effectively load biological molecules to improve the transfection thereof.

BRIEF DESCRIPTION OF THE INVENTION

The authors of the invention have designed and produced different polyphosphazenes which are suitable for the transfection of biological molecules.

In that sense, in a first aspect, the invention relates to a polyphosphazene comprising:

- at least one hydrocarbon chain (A) of between 6 and 24 members, wherein between 1 and 4 members are heteroatoms independently selected from O, N and S, and the end of the chain is a linear or branched $C_1$-$C_6$ alkyl group, optionally the hydrocarbon chain has between 1 and 3 substituents independently selected from hydroxyl and thiol; and,
- at least one hydrocarbon chain (B) of between 6 and 24 members, wherein between 1 and 4 members are heteroatoms independently selected from O, N and S, and the terminal group of the chain is a group of formula $—NH_2$.

Furthermore, the polyphosphazenes of the invention are capable of forming complexes with biological molecules. Furthermore, in that sense, a second aspect of the invention relates to a complex comprising a polyphosphazene of the first aspect of the invention and a biologically active molecule.

In other aspects, the invention relates to the use of the polyphosphazene or of the complex of the invention, a pharmaceutical composition, a kit and a method for producing same.

DETAILED DESCRIPTION OF THE INVENTION

Figure 1:
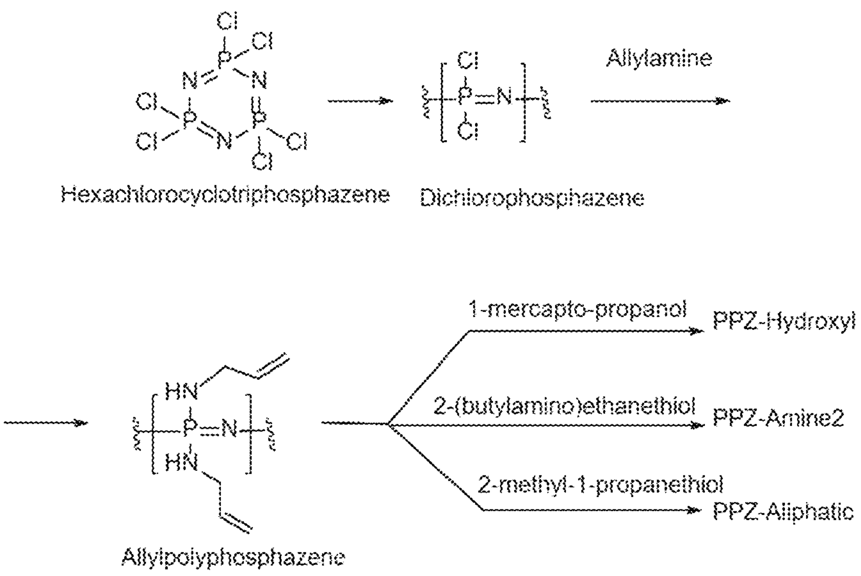
FIG. 1. Scheme of the synthesis and modification of the polyphosphazene precursor by means of thiol-ene chemistry.

As mentioned above, in a first aspect, the invention relates to a polyphosphazene comprising:

- at least one hydrocarbon chain (A) of between 6 and 24 members, wherein between 1 and 4 members are heteroatoms independently selected from O, N and S, and the end of the chain is a linear or branched $C_1$-$C_6$ alkyl group, optionally the hydrocarbon chain has between 1 and 3 substituents independently selected from hydroxyl and thiol; and,
- at least one hydrocarbon chain (B) of between 6 and 24 members, wherein between 1 and 4 members are heteroatoms independently selected from O, N and S, and the terminal group of the chain is a group of formula —$NH_2$.

Each monomer unit of polyphosphazene can be represented by the following formula:

(I)

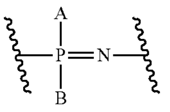

such that the phosphorus atom is attached to a type (A) chain and to a type (B) chain. In a particular embodiment, the polyphosphazenes of the invention have between 150 and 600 monomer units. In a more particular embodiment, the polyphosphazenes of the invention have between 200 and 500 monomer units.

For the present invention, "hydrocarbon chain of between 6 and 24 members" is understood to mean a hydrocarbon which has between 6 and 24 carbon atoms in its backbone and can be linear or branched. Between 1 and 4 carbon atoms of these hydrocarbon chains may have been substituted by heteroatoms. In that sense, in the hydrocarbon chains there can be 1, 2, 3 or 4 heteroatoms which are part of the chain, taking the place of a member. Said heteroatoms are selected from O, N and S. Preferably, the hydrocarbon chains have between 6 and 16 members. Preferably, 2 or 3 members of the hydrocarbon chains are heteroatoms independently selected from N and S.

For the present invention, "substituent" is understood to mean a group of atoms having a chemical function, i.e., a functional group, which is attached to the hydrocarbon chain in one of its positions but is not part of said chain.

For the present invention, the "end of the chain" is understood to mean the final part of the hydrocarbon chain (A), with the beginning of said end of the chain being the member following the heteroatom immediately preceding the end, or in other words, the heteroatom located as the member farthest away from the phosphorus atom.

For the present invention, "terminal group" is understood to mean a group of atoms having a chemical function, i.e., a functional group, which takes up the position at the end of the hydrocarbon chain.

The polyphosphazenes of the invention are characterized in that they comprise a hydrocarbon chain (A) the alkyl group of which at the end of the chain is an aliphatic and hydrophobic group. The presence of hydrophobic groups in the polymer has the advantage of improving the diffusion thereof through cell membranes.

In a particular embodiment, the hydrocarbon chain (A) has the following structure:

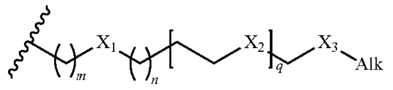

wherein m can have the value 0, 1 or 2,
n can have the value 1, 2 or 3,
q can have the value 0 or 1,
each $X_1$, $X_2$ and $X_3$ are independently selected from the NH, S and O atoms,
Alk is a linear or branched $C_1$-$C_6$ alkyl, optionally having a substituent selected from a hydroxyl or thiol group. Alk is what has been referred to above as the end of the chain. Preferably, methyl, ethyl, propyl, iso-propyl, butyl, iso-butyl and tert-butyl.

In a particular embodiment, these hydrocarbon chains (A) have a heteroatom at position 1 of the chain, more particularly said heteroatom is N. In another particular embodiment, the hydrocarbon chains (A) have a heteroatom at position 5, more particularly said heteroatom is S. In another particular embodiment, the hydrocarbon chains (A) have two heteroatoms in the chains, with an N at position 1 and an S at position 5.

In a particular embodiment, the hydrocarbon chains (A) of the polyphosphazenes of the invention are selected from the group consisting of:

1

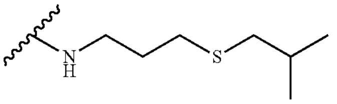

2

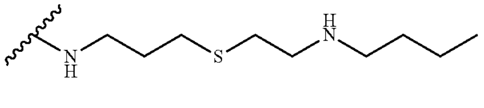

-continued

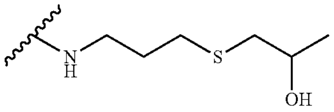

3

The polyphosphazenes of the invention also are characterized in that they comprise a hydrocarbon chain (B) with an —$NH_2$ terminal group. This terminal group has the advantage of increasing protein or nucleic acid loading capacity by means of electrostatic interaction.

In a particular embodiment, these hydrocarbon chains (B) have a heteroatom at position 1 of the chain, more particularly said heteroatom is N. In another particular embodiment, the hydrocarbon chains (B) have a heteroatom at position 5, more particularly said heteroatom is S. In another particular embodiment, the hydrocarbon chains (B) have two heteroatoms in the chains, with an N at position 1 and an S at position 5.

The presence of hydrocarbon chains (A) and (B) with the technical features described above in the polyphosphazenes of the invention favors the loading capacity and the internalization of biologically active molecules, and the final effect is that a much more efficient transfection is obtained.

Furthermore, the polyphosphazenes of the invention form complexes with biologically active molecules. In that sense, in a second aspect, the invention relates to a complex comprising a polyphosphazene as described above, and a biologically active molecule.

In a particular embodiment, the complexes of the invention have a particle size of between nm and 300 nm, preferably between 80 nm and 200 nm. In a particular embodiment, the complexes of the invention have a surface charge of between +20 mV and +50 mV.

In a particular embodiment, the biologically active molecule is selected from a protein and a polynucleotide. In a more particular embodiment, the biologically active molecule is a plasmid encoding BMP-4.

Furthermore, the complexes of the invention can also incorporate an anionic polyphosphazene.

For the present invention, "anionic polyphosphazene" is understood to mean that polyphosphazene having anionic groups, for example, carboxylic groups.

In a particular embodiment, the anionic polyphosphazene comprises a hydrocarbon chain of between 6 and 24 members, wherein between 1 and 4 members are heteroatoms independently selected from O, N and S, and at least one carboxylic group.

Figure 2:
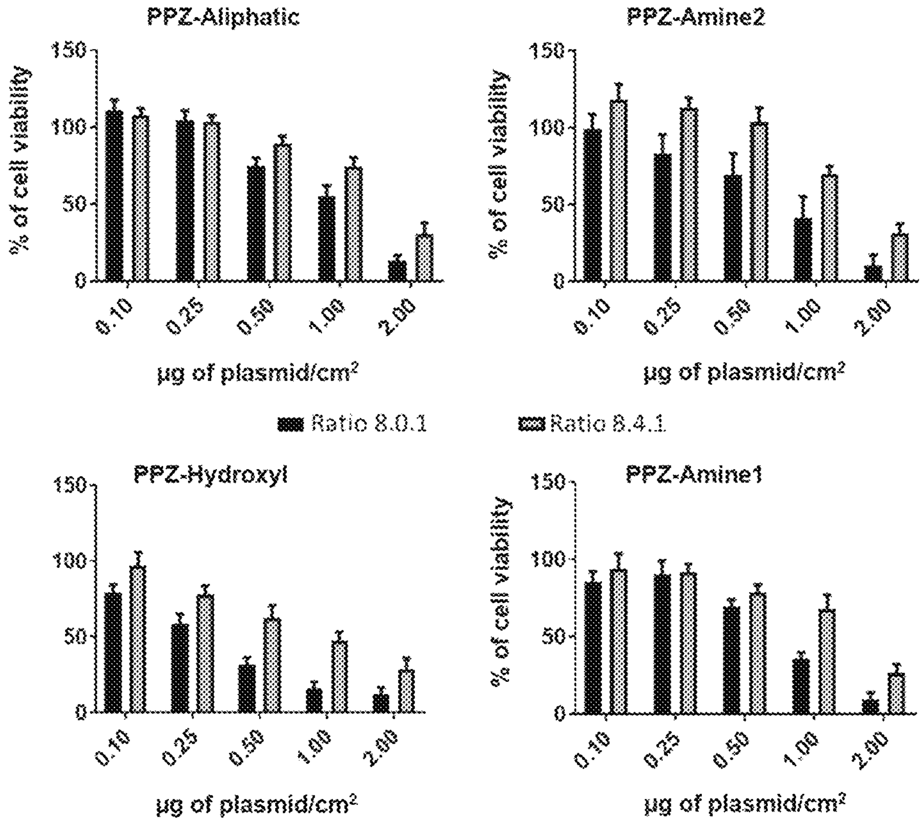
FIG. 2. Cellular metabolic activity of the commercial line which corresponds to human glioblastoma (U87MG) and which has been treated with different concentrations of nanocomplexes (ratio of 8.0.1 and 8.4.1) 48 hours after treatment. Concentrations are expressed in μg of plasmid to compare the toxicities of the formulations with the same loading capacity.

The complexes of the invention which further comprise anionic polyphosphazenes have the advantage of being less toxic as demonstrated in Example 3.1. and FIG. 2. Furthermore, these complexes have greater transfection capacity, as demonstrated in Example 4 and FIG. 3. PPZ-Aliphatic has the highest transfection capacity.

In a preferred embodiment, the invention relates to a complex comprising a polyphosphazene of the invention, an anionic polyphosphazene and a biologically active molecule. In a more preferred embodiment, the invention relates to a complex comprising a polyphosphazene of the invention the type (A) chain of which has formula 1.

In a particular embodiment, the complexes of the invention further comprise a chemotherapeutic molecule. In a more particular embodiment, the chemotherapeutic molecule is temozolomide.

In another aspect, the invention relates to a pharmaceutical composition comprising the complex of the invention and pharmaceutically acceptable excipients.

In another aspect, the invention relates to the polyphosphazenes of the invention or the pharmaceutical composition of the invention for use thereof in medicine.

In a particular embodiment, the invention relates to the polyphosphazenes of the invention or the pharmaceutical composition of the invention for use thereof in gene therapy or oncology, or for use thereof in the treatment of brain tumors, preferably glioblastomas.

In another aspect, the invention relates to a kit comprising at least two containers wherein one of the containers comprises a complex of the invention, and the other container comprises a chemotherapeutic molecule, together with instructions for use thereof in the treatment of a disease for sequential or simultaneous administration of both ingredients.

In another embodiment, the invention relates to the use of the complex of the invention in the preparation of vectors for transporting biologically active molecules.

Materials and Methods

All of aluminum chloride (99.99%), anhydrous tetrahydrofuran (THF), cysteamine (Cys), deuterated chloroform (99.96 atom % D contains 0.03% TMS), deuterium oxide (99.9 atom % D contains 0.05 wt % of 3-(trimethylsilyl) propionic-2,2,3,3-d4 acid), heparin in the form of sodium salt (from porcine intestinal mucosa), HEPES (≥99.5%), hexachlorocyclotriphosphazene (99%), potassium chloride (BioXtra≥99%), triethylamine (TEA), Tris-Acetate-EDTA buffer solution (10×), 1-mercapto-2-propanol (MP), 2-(butylamino)ethanethiol (BET), 2-(dimethylamino)ethanethiol hydrochloride (DMAES), 2,2,2-trifluoroethanol (TFE), 2,2-dimethoxy-2-phenylacetophenone (DMPA), 2-methyl-1-propanethiol (MPT), 6-mercaptohexanoic acid (6MHA), temozolomide, xylazine were purchased form Sigma-Aldrich. Ketamine for anesthesia was ordered from Pfizer. Ethanol, crystal violet and glacial acetic acid were acquired from Merck. DNase/RNase-free water (Invitrogen), Dulbecco's modified eagle medium (DMEM) (Gibco), OptiMEM (Gibco), Eagle's minimum essential medium (EMEM), fetal bovine serum (FBS) (Gibco), penicillin-streptomycin for culture medium (Gibco), dialysis membrane (pore size of 7 kDa), Lipofectamine 2000 transfectant agent (Life Technologies), SYBR® Gold nucleic acid dye (Life Technologies) were acquired from Thermo Fisher. The Bio-Rad protein determination test was purchased from BioRad (CA, USA). The Roche luciferase determination test (Germany), MTS BioVision cell proliferation determination kit (USA), Alamar Blue Promega (Spain). Bone morphogenetic protein 4 (BMP-4) was purchased from Preprotech (United Kingdom). The plasmid expressing BMP4 comes from Sino Biological Inc. (Germany).

Example 1. Preparation of Cationic Polyphosphazenes and Anionic Polyphosphazene

1.1. Synthesis of the poly(allylamino-phosphazene) Precursor

The precursor was synthesized following the protocol developed by Dr. Wei-Hsin Hsu (Hsu, W.-H., Sánchez-Gómez, P., Gomez-Ibarlucea, E., Ivanov, D. P., Rahman, R., Grabowska, A. M., Garcia-Fuentes, M. (2019). Structure-Optimized Interpolymer polyphosphazene Complexes for Effective Gene Delivery against Glioblastoma. *Advanced Therapeutics,* 2(3), 1800126. https://doi.org/10.1002/adtp.201800126). In a previously dried flask, 14.4 mmol of hexachlorocyclophosphazene were mixed with 7.5% (w/w) aluminum chloride (catalyst) in an inert nitrogen atmosphere and heated to 240-250° C. for 3 hours, aluminum chloride caused polymerization after ring opening and removal of part of the chlorides, yielding the product dichlorophosphazene. Then, the product was cooled to 120° C. and solubilized in diglyme to minimize cross-linking and prevent the product from solidifying and centrifuged to remove aluminum chloride (−10° C., 7000 G, 5 min). The supernatant was transferred to a flask with THF, TEA (3 equivalents/chlorine) and allylamine (3 equivalents/chlorine), the reaction was kept in an ice bath for 24 hours and then at room temperature for 24 hours. The resulting product was filtered to remove TEA hydrochloride and precipitated with water, then centrifuged (4° C., 7000 G, 10 min), and the precipitate was collected and vacuum dried overnight (FIG. 1). Allylphosphazene (APPZ) was characterized by phosphorus, proton, and DOSY magnetic resonance.

1.2. Modification of the Precursor by Means of Thiol-Ene Chemistry

The side chains of the precursor were modified by means of thiol-ene chemistry to introduce different radicals, the thiol group of the new compounds reacts with the allyl group of the precursor, obtaining five different polyphosphazenes.

The product obtained above was dissolved in trifluoroethanol (TFE) and mixed with the desired substituent or substituents in the following proportion: 3 equivalents/allyl group. The substituents used were: 1-mercapto-2-propanol (to obtain polyphosphazene PPZ-Hydroxyl), 2-(butylamino) ethanethiol (to obtain polyphosphazene PPZ-Amine2), 2-methyl-1-propanethiol (to obtain polyphosphazene PPZ-Aliphatic). The mixture was bubbled with nitrogen to achieve an inert atmosphere and the catalyst 2,2-dimethoxy-2-phenylacetophenone (DMAES) (0.05 equivalents/allyl group) was added. The reaction took place for 3 hours with magnetic stirring and UV irradiation ($\lambda$=365 nm) (FIG. 1). Then, the product was dialyzed (membrane pore size of 7 kDa) against 2 mM HCl for 24 hours and against water for 48 hours. The dialysate was lyophilized and the compounds were characterized by phosphorus and proton, COSY and HSQC NMR.

The polyphosphazene PPZ-Amino1 was also synthesized to allow comparing same with the polyphosphazenes of the invention. This polyphosphazene was prepared as indicated above and using cysteamine as a reagent to react with allylphosphazene.

An anionic polyphosphazene (PPZ-anionic) was also synthesized using 6-mercaptohexanoic acid as a substituent, using a proportion of 3 equivalents of mercaptohexanoic acid/allyl group to react with allylphosphazene, following the instructions described above.

The percentages of substitution of each substituent in the heteropolymers is 50% for PPZ-Aliphatic. However, for PPZ-Amine2, the substitution is 68% for the cysteamine radical and 32% for the 2-(butylamino)ethanethiol radical, and in the case of PPZ-Hydroxyl, the substitution was 33% for the cysteamine radical group and 66% for the 1-mercapto-2-propanol radical.

To determine the molar mass of the polymers, they were dissolved in 10 mM sodium chloride at a concentration of 5 mg/mL and measured by means of asymmetric flow field-flow fractionation (AF4) using AF2000 MultiFlow equipment coupled to a multi-angle light scattering (MALS) detector (Postnova, Germany). The detector was calibrated with a standard consisting of bovine serum albumin monomers (66 kDa) and quality control was performed everyday by means of pullulan (48.8 kDa).

TABLE 1

Molar mass of the polymer and distribution measured by means of AF4.

| | Mw (g/mol) | Mn (g/mol) | Đ |
|---|---|---|---|
| PPZ-Aliphatic | $1.48 \pm 0.01 \times 10^5$ | $1.08 \pm 0.1 \times 10^5$ | 1.37 |
| PPZ-Amine2 | $1.10 \pm 0.1 \times 10^5$ | $7.98 \pm 0.5 \times 10^4$ | 1.37 |
| PPZ-Hydroxyl | $8.18 \pm 0.1 \times 10^4$ | $6.5 \pm 0.9 \times 10^4$ | 1.26 |
| PPZ-Anionic | $6.16 \pm 0.3 \times 10^4$ | $5.11 \pm 0.2 \times 10^4$ | 1.21 |
| PPZ-Amine1 | $1.19 \pm 0.1 \times 10^5$ | $8.83 \pm 1.3 \times 10^4$ | 1.35 |

Mw: weight average molecular weight;
Mn: number average molecular weight;
Đ: polydispersity index.

Example 2. Formation of Nanocomplexes

Example 2.1. Formation of the Nanocomplex with a Plasmid

Nanocomplexes were prepared by means of ionic complexation using a model plasmid encoding enhanced green fluorescent protein (eGFP) and luciferase (Luc). The polymers were dissolved in 10 mM HEPES (pH 5.5) and the plasmid was dissolved in water. The formation of complexes takes place by means of ionic complexation when the plasmid, or the plasmid-anionic polymer mixture, is added to the cationic polymer solution with magnetic stirring. Different loading ratios have been prepared, in the case of nanocomplexes containing only the cationic polymer, the ratios are based on the number of positively charged amines of the cationic polymer (N) and negatively charged phosphates of the plasmid (F), in the case of nanocomplexes also containing the anionic polymer, the ratios were established between the number of positively charged amines of the cationic polymer (N), the number of negatively charged carboxyl groups of the anionic polymer (C) and the number of negatively charged phosphate groups of cDNA (F), therefore N/F and N/C/F, respectively. The nanocomplexes were prepared for a final encapsulated plasmid concentration of 25 µg/mL to thereby allow comparing the formulations with one another, all of them having the same amount of plasmid.

Characterization of the Size, Surface Charge and Concentration of Nanocomplexes

The size of the nanocomplexes was characterized using dynamic light scattering (DLS) and Zeta potential was determined by means of laser doppler anemometry using a Nanosizer ZS instrument (Malvern, United Kingdom). Each analysis was performed in triplicate at 25° C. with a backscattering angle of 173°. Nanocomplex concentration was determined by means of the nanocomplex monitoring analysis using a Nanosight NS300 system (Malvern Instruments, Worcestershire, United Kingdom) equipped with a laser measuring at $\lambda$=488 nm, after diluting the samples 1:400 in 10 mM HEPES. In the case of Zeta potential, measurements were performed with a 1:10 dilution in 1 mM KCl.

TABLE 2

Characterization of cationic nanocomplexes by means of size and surface charge.

| | Nanocomplexes (N:F) | Size (nm) | PDI | Surface charge (mV) |
|---|---|---|---|---|
| PPZ-Aliphatic | 4:1 | 131 ± 2 | 0.2 | +46 ± 3 |
| | 8:1 | 141 ± 4 | 0.2 | +54 ± 1 |
| | 16:1 | 149 ± 6 | 0.3 | +54 ± 2 |
| PPZ-Amine2 | 4:1 | 96 ± 7 | 0.2 | +48 ± 3 |
| | 8:1 | 110 ± 5 | 0.1 | +53 ± 4 |
| | 16:1 | 122 ± 5 | 0.2 | +56 ± 2 |
| PPZ-Hydroxyl | 4:1 | 101 ± 3 | 0.1 | +31 ± 2 |
| | 8:1 | 116 ± 2 | 0.1 | +34 ± 4 |
| | 16:1 | 117 ± 3 | 0.1 | +41 ± 3 |
| PPZ-Amine1 | 4:1 | 110 ± 7 | 0.2 | +46 ± 2 |
| | 8:1 | 129 ± 7 | 0.1 | +51 ± 1 |
| | 16:1 | 128 ± 5 | 0.2 | +54 ± 1 |

nm: nanometers;
PDI: polydispersity index;
mV: millivolts.

The polymer:plasmid ratio affects the size and the surface charge of the nanocomplexes. When the proportion of cationic polymers increases, the surface charge of the nanocomplexes increases slightly, being positive in all cases; with respect to size, a small variation can be observed although all the prototypes showed a size of between 100 and 150 nm, which makes them suitable gene therapy vectors.

TABLE 3

Characterization of cationic and anionic nanocomplexes by means of size and surface charge, and concentration.

| N.C.F proportion | Size (nm) | PDI | Surface charge (mV) | Concentration (particles/mL) |
|---|---|---|---|---|
| PPZ-Aliphatic 8.0.1 | 150 ± 4 | 0.2 | +38 ± 3 | $5.45 \pm 0.1 \times 10^{10}$ |
| PPZ-Aliphatic 8.4.1 | 143 ± 4 | 0.2 | +32 ± 3 | $1.69 \pm 0.05 \times 10^{11}$ |
| PPZ-Amine2 8.0.1 | 126 ± 4 | 0.2 | +37 ± 4 | $6.94 \pm 0.3 \times 10^{10}$ |
| PPZ-Amine2 8.4.1 | 129 ± 3 | 0.1 | +31 ± 3 | $1.55 \pm 0.04 \times 10^{11}$ |
| PPZ-Hydroxyl 8.0.1 | 111 ± 3 | 0.1 | +38 ± 2 | $7.22 \pm 0.3 \times 10^{10}$ |
| PPZ-Hydroxyl 8.4.1 | 135 ± 3 | 0.1 | +39 ± 3 | $1.71 \pm 0.05 \times 10^{11}$ |
| PPZ-Aminel 8.0.1 | 119 ± 2 | 0.2 | +36 ± 2 | $5.29 \pm 0.2 \times 10^{10}$ |
| PPZ-Aminel 8.4.1 | 122 ± 2 | 0.1 | +35 ± 4 | $1.62 \pm 0.08 \times 10^{11}$ |

nm: nanometers;
PDI: polydispersity index;
mV: millivolts.

The size of all the nanocomplexes formed is between 100 and 150 nm, the surface charge is between +30 and +40 mV, and it was observed that the concentration of nanocomplexes associating the cationic polymers and the anionic polymer is between 2 and 3 times greater than those containing only cationic polymers.

Morphology analysis was performed by means of field emission scanning electron microscopy (FESEM) with energy dispersive X-ray spectroscopy (Zeiss Gemini Ultra Plus, Germany) and using a scanning transmission electron microscope (STEM) and immersion lens detectors (InLens) for sample observation. For sample preparation, 10 μL of the nanocomplexes were placed on a copper grating with carbon films and excess was removed. The same volume of phosphotungstic acid (2%) was then added and washed with water twice. Once dry, the sample was observed through STEM detectors and immersion lenses (InLens).

In all cases, the particles are spherical and those containing anionic polymer show a higher intensity, which can be indicative of a higher particle density compared to cationic ones.

Association Efficiency of Nucleic Acid in the Nanocomplexes

Nanocomplex-binding efficiency was determined by means of an agarose gel delay assay. The samples were loaded in agarose gel (1% w/v in Tris-EDTA buffer 1×). Each well contained 0.33 μg of cDNA, free plasmid was used as control. For sample visualization and to facilitate loading, all the samples contained 1×SYBR® Gold for nucleic acid staining and a loading buffer (30% glycerol and 0.25% bromophenol blue). The disassociation assay was performed by incubating samples with an excess of anionic competitor (20:1 w/w of heparin:cDNA) for 1 hour at 37° C.

It was demonstrated that the nucleic acid does not bind irreversibly to the vehicle and can be released into the physiological medium and perform its function.

Example 2.2. Formation of the Nanocomplex with a Protein

Nanocomplexes were prepared by means of ionic complexation using a model protein, heparin. The polymers were dissolved in 10 mM HEPES (pH 5.5) and the protein was dissolved in water. The formation of the complexes takes place by means of ionic complexation when the protein, or the protein-anionic polymer mixture, is added to the cationic polymer solution with magnetic stirring.

The size, the polydispersity index (PDI), and the charge of the prepared nanocomplexes were measured.

TABLE 4

Characterization of cationic and anionic nanocomplexes by means of size and surface charge.

| Mass ratio (PPZ-Aliphatic: PPZ-Anionic-heparin) | Size (nm) | PDI | Surface charge (mV) |
|---|---|---|---|
| 8.0.1 | 137 ± 3 | 0.2 | +39 ± 2 |
| 8.0.2 | 136 ± 4 | 0.2 | +40 ± 1 |
| 8.3.1 | 142 ± 3 | 0.2 | +42 ± 3 |
| 8.3.2 | 155 ± 12 | 0.3 | +24 ± 1 |

nm: nanometers;
PDI: polydispersity index;
mV: millivolts.

Example 3. Toxicity Studies

3.1. 2D In Vitro Toxicity

All in vitro assays were performed in human glioblastoma cells U87MG cultured in DMEM (Gibco, USA) supplemented with 10% fetal bovine serum (FBS) (Gibco, USA) and 1% penicillin/streptomycin (P/S) (Gibco, USA) by incubating them at 37° C. under moisture saturated atmosphere and 5% $CO_2$. In all assays, the negative control is the medium and the positive control is 0.1% Triton.

For the 2D toxicity assay, 8000 cells/well were seeded in a 96-well plate and incubated for 24 hours before treatment to allow the cells to adhere to the bottom of the well. Then, the nanocomplexes were incubated in supplemented medium for 4 hours at different reference concentrations with respect to plasmid concentration (0.1-2 μg/$cm^2$). Then, the cells were washed with PBS, fresh medium was added, and the cells were left to grow for another 48 hours. Cytotoxicity evaluation was performed by adding 10 μl of MTS per well (BioVision, USA) and absorbance was measured after 3 hours of incubation in a plate reader at 495 nm.

FIG. 2 shows that, in all cases, there was a decrease in the toxicity of the nanocomplexes containing the anionic polymer compared to those only containing the cationic polymer.

3.2. 3D In Vitro Toxicity

For the 3D toxicity assay, neurospheres were first formed, 500 cells/well were seeded in an ultralow adherence 96-well plate, the cells were centrifuged for 20 minutes at 200 rcf. After 3 days, the nanocomplexes were incubated for 12 hours at a nanocomplex concentration relative to 2 μg of plasmid/ml; after 12 hours, the nanocomplexes were replaced with fresh medium and the neurospheres were incubated for another 72 hours. Two parameters were evaluated: the size of the neurosphere after 0, 24, 48 and 72 hours and cytotoxicity after 72 hours by means of resazurin reduction metabolic assay (CellTiter-Blue®, Promega, USA). For the metabolic assay, 40 μl of the reagent were added per well and incubated for 4 hours. Fluorescence was evaluated using a plate reader at an excitation wavelength of 539 nm and an emission wavelength of 620 nm.

Similar growth and morphology were observed in untreated neurospheres (viability control by adding fresh culture medium) and neurospheres treated with the formulations, whereas disaggregation and a decrease in size were observed in neurospheres treated with triton (toxic control). Moreover, a metabolic test was also performed with Alamar blue and it has been shown that the formulations are not toxic at said concentration, data which is consistent with that obtained in the neurosphere growth evolution study.

Example 4. In Vitro Transfection Studies

Glioblastoma cell line U87MG was used for the transfection assay in which 56,000 cells/well were seeded in a 24-multiple well plate in DMEM supplemented with 10% FBS and 1% P/S. After 24 hours, nanocomplexes were added at a concentration of 0.5 μg of plasmid/cm 2 in OptiMEM (Gibco, USA) and incubated for 4 hours. Then, they were washed and replacement with fresh DMEM was performed, and the cells were incubated for 48 hours. The Luciferase Reporter Gene Assay commercial kit (Roche, Germany) was used to measure transfection. The cells were washed twice with PBS and 100 μl of lysis buffer were added, the lysate was centrifuged after 5 minutes. 50 μl of the supernatant were placed in a blank plate, and using an automatic injector, 25 μl of luciferin from the commercial kit were added immediately before each luminescence measurement in a Mithras LB940 luminometer (Berthold, Germany). The results were corrected for protein by means of the Bio-Rad protein assay (BioRad, USA). 40 μL of the reagent were added to the sample and absorbance was measured at 595 nm.

Figure 3:
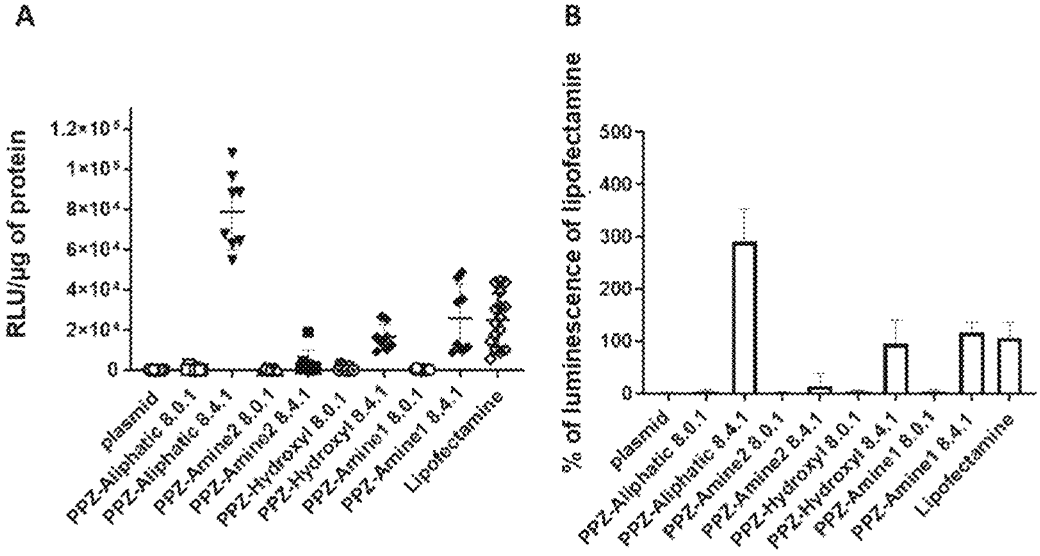
FIG. 3. Transfection in two-dimensional cultures of human glioblastoma cell line (U87MG) measured by luminescence 48 hours after transfection and after adding the substrate luciferin. Results are expressed with respect to the luminescence of lipofectamine (transfection control).

FIG. 3 (results are expressed as the percentage of luminescence of lipofectamine) shows that 48 hours after treatment, the prototypes containing the anionic polymer have shown a marked increase in transfection compared to the cationic prototypes and the free plasmid. The luminescence obtained after transfection with PPZ-Aliphatic combined with PPZ-Anionic was greater even compared to the commercial transfectant, lipofectamine.

Example 5. Zebrafish Embryo Acute Toxicity (FET) Studies

OECD guidelines were followed for this test; newly fertilized zebrafish eggs were selected about 2-3 hours after fertilization, specifically the eggs were selected in the 16-32 cell blastomere stages. Ten viable fertilized eggs were placed in osmosis water per group, one per well. The embryos were incubated with different concentrations of polymers forming the nanocomplexes at 26±1° C. for 96 hours and toxicity was observed every 24 hours until the end of the test. The observations made for determining toxicity include the detection of embryo coagulation, lack of somite formation, tail detachment, lack of heartbeats (after 48 hours) and edema in the embryo.

The formulations were diluted in reverse osmosis water at different concentrations in order to compare the toxicity of the nanocomplexes. The embryos were incubated for 96 hours and their evolution was studied every 24 hours until the end of the study. The mortality of the negative control was less than 10% and the hatch rate was above 80%. To express toxicity results, the parameters listed in the following table were calculated; Lethal concentration needed for killing 50% of the population (LC50); No observed effect concentration (NOEC); Lowest observed effect concentration (LOEC).

In all cases, LC50 is greater in prototypes containing the anionic polymer, furthermore the results coincide with the trend found in vitro. The results showed that the aliphatic polymer is the least toxic, but it should be considered that for the same plasmid load, the concentration of the aliphatic polymer almost doubles that of PPZ-Amine1 or PPZ-Amine2, due to the number of amine groups per monomer.

TABLE 5

In vivo toxicity determined by means of zebrafish embryo acute toxicity test (FET). The results are expressed in mg of cationic polymer/mL of osmosis water.

| | LC50 (mg/l) | NOEC | LOEC |
|---|---|---|---|
| PPZ-Aliphatic 8.0.1 | >10 | <1 | <1 |
| PPZ-Aliphatic 8.4.1 | 16.052 | 10 | 20 |
| PPZ-Amine2 8.0.1 | 5.854 | 2.5 | 5 |
| PPZ-Amine2 8.4.1 | >10 | 7.5 | 10 |
| PPZ-Hydroxyl 8.0.1 | 5.886 | 2.5 | 5 |
| PPZ-Hydroxyl 8.4.1 | 9.647 | 5 | 7.5 |
| PPZ-Amine1 8.0.1 | 5.521 | 1 | 2.5 |
| PPZ-Amine1 8.4.1 | 9.98 | 10 | 20 |

LC50: lethal concentration needed for killing 50% of the population;
NOEC: No observed effect concentration;
LOEC: Lowest observed effect concentration.

Example 6. Preparation of Nanocomplexes with Plasmid Encoding BMP-4

Nanocomplexes were prepared by means of ionic complexation using the cationic polymer PPZ-Aliphatic associated with PPZ-Anionic, in this case, nanocomplexes were prepared for a final encapsulated plasmid concentration of 83.3 μg of plasmid/mL, which corresponds with a theoretical nanocomplex concentration of 0.967 mg/mL. In this case, plasmid encoding bone morphogenetic protein 4 (BMP4) was used as nucleic acid and nanocomplexes associated with a non-therapeutic plasmid, pEGFP-Luc, used in formulation optimization, were used as blank nanocomplexes.

The size of the nanocomplexes was determined by means of dynamic light scattering (DLS) using a Nanosizer ZS instrument (Malvern, United Kingdom) after a 1:10 dilution in 1 mM KCl. Each analysis was performed in triplicate at 25° C. with a back-scattering angle of 173°.

| | Size (nm) | PDI |
|---|---|---|
| Blank NCs | 143 ± 4 | <0.2 |
| NCs-BMP-4 | 125 ± 3 | <0.2 |

Nucleic acid complexation efficiency was evaluated using the same technique described in Example 2, and no changes were observed in nucleic acid association/disassociation, which demonstrates that more concentrated particles can be prepared without affecting their physicochemical properties.

Example 7. Clonogenicity Assay

Two human glioblastoma cell lines (U87MG and U251) were used in this experiment. Both cell lines were cultured in supplemented EMEM, $10^5$ cells/well were seeded in a 12-well plate. After 24 hours, treatment was added, the cells were treated with seven different treatments: medium, BMP4 protein, blank nanocomplexes (blank NCs), nanocomplexes with BMP-4 (NCs-BMP4) prepared in Example 6, temozolomide (Tz), combination of BMP4 protein+Tz and combination of NCs-BMP4+Tz. The concentration was 23.2 µg of nanocomplexes/ml, 30 ng of BMP4 protein/ml and 2.4 µg of temozolomide/ml. Two days later, 500 cells/well were re-seeded in a 6-well plate and left to grow for another 12 days.

The cells were stained with a preparation of 50% ethanol, 5% acetic acid and 0.5% crystal violet, washed with water twice, and the number of colonies per well was counted.

Figure 4:
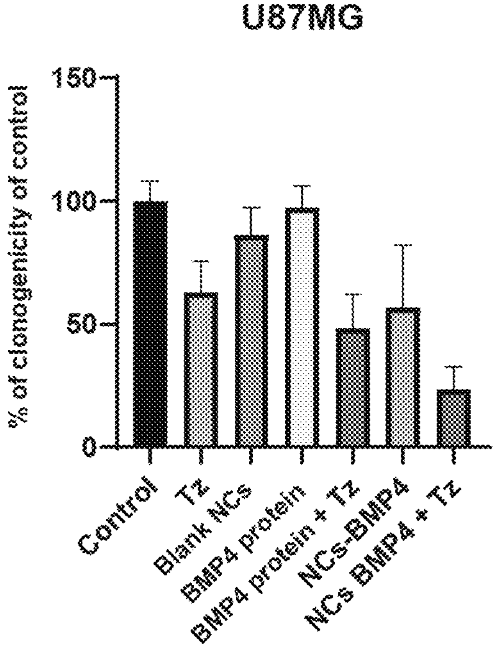
FIG. 4. Clonogenicity assay in two glioblastoma cell lines (U251 and U87MG). The clonogenic capacity of the cells was studied after a 48-hour incubation with different treatments, the data is expressed in number of colony forming units per plate (untreated cells were assumed to be 100%); Tz: temozolomide; NCs: nanocomplexes; BMP4: Bone morphogenetic protein ($p<0.05$).

FIG. 4 shows that, in both cell lines, nanocomplexes with BMP4 reduce tumor cell clonogenicity compared to the direct administration of the protein or blank nanocomplexes; furthermore, the association thereof with temozolomide generates a synergistic effect compared to that observed when the chemotherapeutic agent is used alone.

Example 8. In Vivo Efficacy in Mouse Glioblastoma Xenograft Model

This experiment was approved by the ethics committee for animal care of Université Catholique de Louvain (2019/UCL/MD004) and was performed according to Belgian National Guidelines in accordance with European Guidelines. The animals had free access to water and food at all times.

Eight week-old nude female NMRI mice (Janvier, France) were anesthetized intraperitoneally with 150 µL of a solution consisting of 10 mg/ml of ketamine (Pfizer, USA) and 1 mg/ml of xylazine (Sigma, USA). Two million fresh U87MG cells were administered subcutaneously in the flank. The tumor was left to grow for ten days before treatment administration.

When the size of the tumor was about 35 $mm^3$, the mice, randomized into six groups, were anesthetized and treatment was administered intratumorally with the exception of temozolamine, which was administered intraperitoneally, using four doses on four consecutive days. Group distribution: Group 1: Control, saline solution (n=7); Group 2: temozolomide (n=6); Group 3: blank nanocomplexes (n=6); Group 4: BMP4 protein+Tz (n=6); Group 5: nanocomplexes-BMP4 prepared in Example 6 (n=7) and Group 6: nanocomplexes-BMP4 prepared in Example 6+Tz (n=7). The administered doses were 5 µg of temozolomide/g of mouse through the intraperitoneal route, 1.54 µg of nanocomplexes with BMP4/g of mouse and 2 ng of BMP4 protein/g of mouse through the intratumor route.

After administering different treatments, the size of the tumor and the body weight of the animals were measured every 2 days. The size of the tumor was measured by means of a digital caliper and the volume was calculated according to the following formula: $V=L\times A\times H$, wherein L is the length, A the width, and H the height of the tumor. Relative tumor volume was calculated as V/Vo (Vo is the tumor volume before the first administration). The mice were deemed dead and sacrificed when the tumor volume was above 1500 $mm^3$, when necrosis or ulcers appeared, when weight loss >20% or when signs of distress were present.

Since there is always a certain heterogeneity in tumor size, the mice were distributed maintaining comparable groups; even so, results were also corrected with respect to the initial tumor volume to reduce variables due to tumor heterogeneity.

Once dissected, the tumors were photographed and the expression of some RNAs involved in the cancer was analyzed. For RNA extraction, the tumors were homogenized in 1 ml of TRI-Reagent (ThermoFisher) by means of the GentleMACS Dissociator (Miltenyi Biotec, Germany), the homogenized tumor was mixed with 200 µl of chloroform/ml of TRI-Reagent and samples were centrifuged, the aqueous phase was transferred to an Eppendorf tube containing 500 µl of isopropanol/mL of TRI-Reagent and cooled to −20° C. The sample was centrifuged and the supernatant decanted, the sediment was washed with ethanol, left to dry at room temperature and resuspended in water. RNA concentration was determined by means of NanoDrop 2000 (ThermoFisher). RNA samples were reverse transcribed using the RevertAid First Strand cDNA Synthesis Kit (ThermoFisher). Real-time PCR (RT-PCR) was performed using the NZYSpeedy qPCR Green Master Mix kit (2×) (NZYTech, Portugal). Both PCRs were carried out using Mastercycler Nexus (Eppendorf, Germany). GAPDH served as the gene for normalizing gene expression. The primer sequences for the genes of interest are shown in the table below.

| | Forward | Reverse |
|---|---|---|
| GAPDH | 5'-GCCAAGGTCATCCATGACAACT-3' (SEQ ID NO: 1) | 5'-AGGGCCATCCACAGTCTTCTG-3' (SEQ ID NO: 2) |
| Sox2 | 5'-ACACCAATCCCATCCACACT-3' (SEQ ID NO: 3) | 5'-GCAAACTTCCTGCAAAGCTC-3' (SEQ ID NO: 4) |
| Nestin | 5'-CCTCCTGGAGGCTGAGAACTC-3' (SEQ ID NO: 5) | 5'-AAGGCTGGCACAGGTGTCTC-3' (SEQ ID NO: 6) |

-continued

| | Forward | Reverse |
|---|---|---|
| Oct4 | 5'-CCCGCCGTATGAGTTCTGTGG-3' (SEQ ID NO: 7) | 5'-CCGGGTTTTGCTCCAGCTTCTC-3' (SEQ ID NO: 8) |
| Nanog | 5'-CCGCGCCCTGCCTAGAAAAGAC-3' (SEQ ID NO: 9) | 5'-AGCCTCCCAATCCCAAACAATACG-3' (SEQ ID NO: 10) |
| BMP4 | 5'-AATGTGACACGGTGGGAAACT-3' (SEQ ID NO: 11) | 5'-CCCGCTGTGAGTGATGCTTA-3' (SEQ ID NO: 12) |
| MDR1 | 5'-AACAACGCATTGCCATAGCTCGTG-3' (SEQ ID NO: 13) | 5'-AGTCTGCATTCTGGATGGTGGACA-3' (SEQ ID NO: 14) |
| MRP1 | 5'-CATCGTTCTGTTTGCTGCCCTGTT-3' (SEQ ID NO: 15) | 5'-AGTACGTGGTGACCTGCAATGAGT-3' (SEQ ID NO:16) |
| ABCG2 | 5'-GCCACGTGATTCTTCCACAA-3' (SEQ ID NO: 17) | 5'-TTCTGCCCAGGACTCAATGC-3' (SEQ ID NO: 18) |

Figure 5:
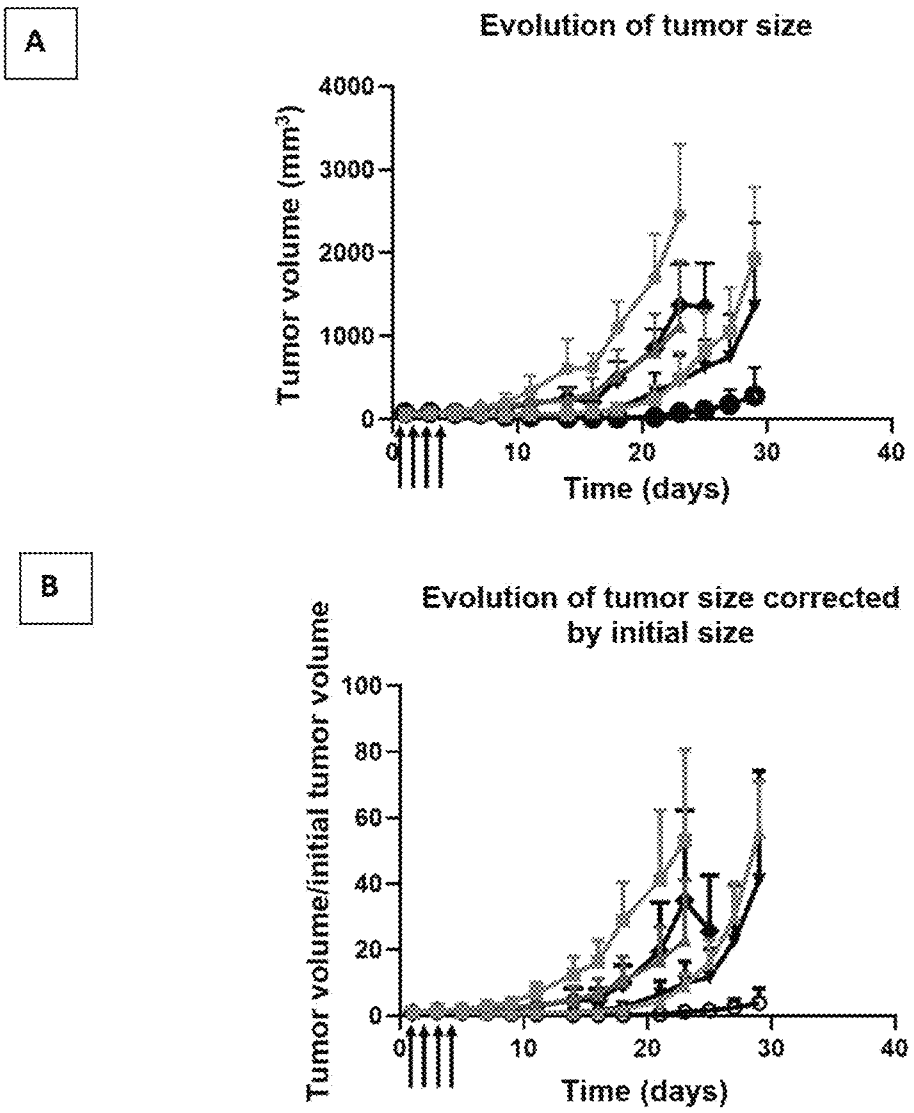
FIG. 5. In vivo efficacy of the formulation alone and in combination with a chemotherapeutic agent. A. Evolution of tumor volume. B. Evolution of tumor volume corrected by the tumor volume before treatment administration. C. Evolution in the weight of mice. D. Percentage of survival of mice taking into account that animals with necrosis in the tumor or a size exceeding 1500 $mm^3$ were sacrificed in order to reduce animal suffering. The red arrows illustrate the four administrations on consecutive days. Legend of the treatment groups: Control (grey circle), Blank nanocomplexes (grey triangle), BMP4 protein+Temozolomide (inverted black triangle), Temozolomide (grey square), Nanocomplexes-BMP4 (black rhombus), Nanocomplexes-BMP4+Temozolomide (black circle).
Figure 5:
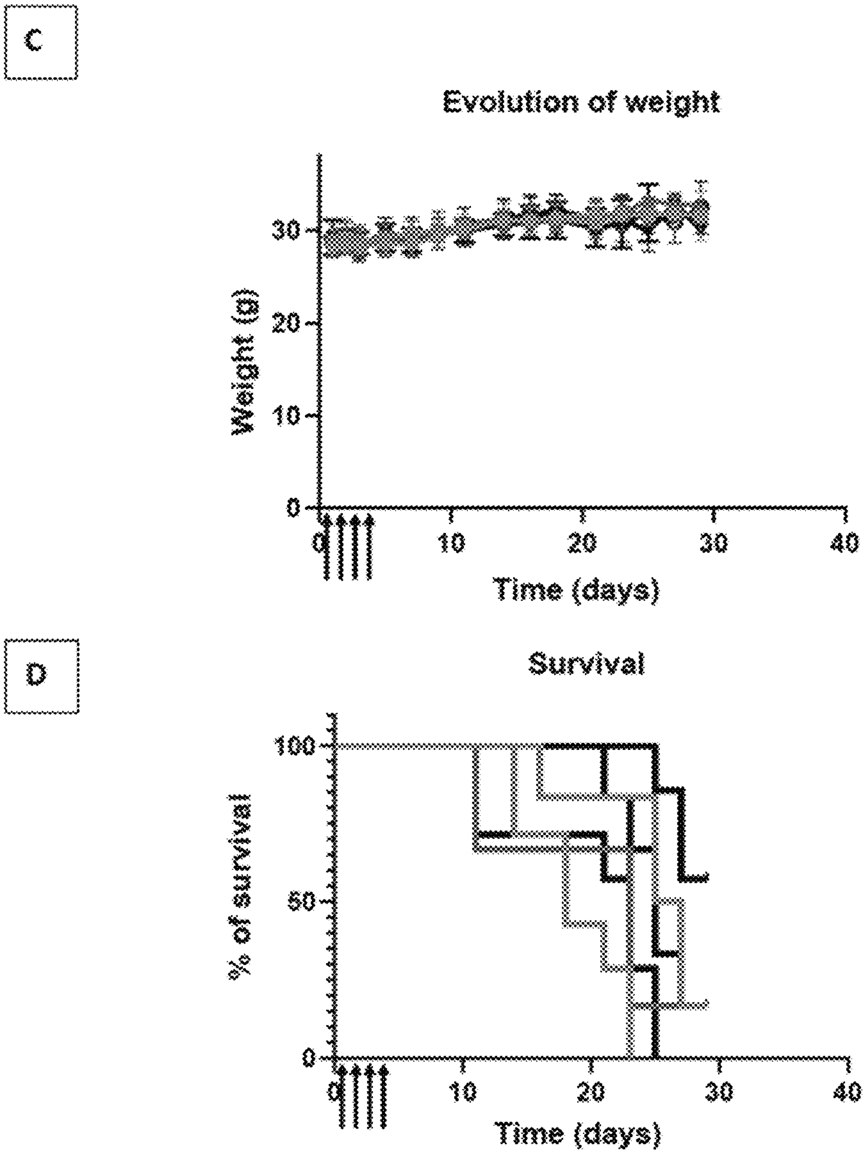

It is observed that the combination of nanocomplexes encoding BMP4 in combination with temozolomide significantly slows down tumor evolution compared to the rest of the groups; it can also be observed that nanocomplexes-BMP4 themselves did not significantly reduce tumor size compared to the control group (FIG. 5*a*).

When the results are corrected taking into account the initial tumor volume, FIG. 5*b*, the same trend as in the preceding graph is observed.

In terms of weight, no toxicity-related weight variations were observed between the different treatments.

Figure 6:
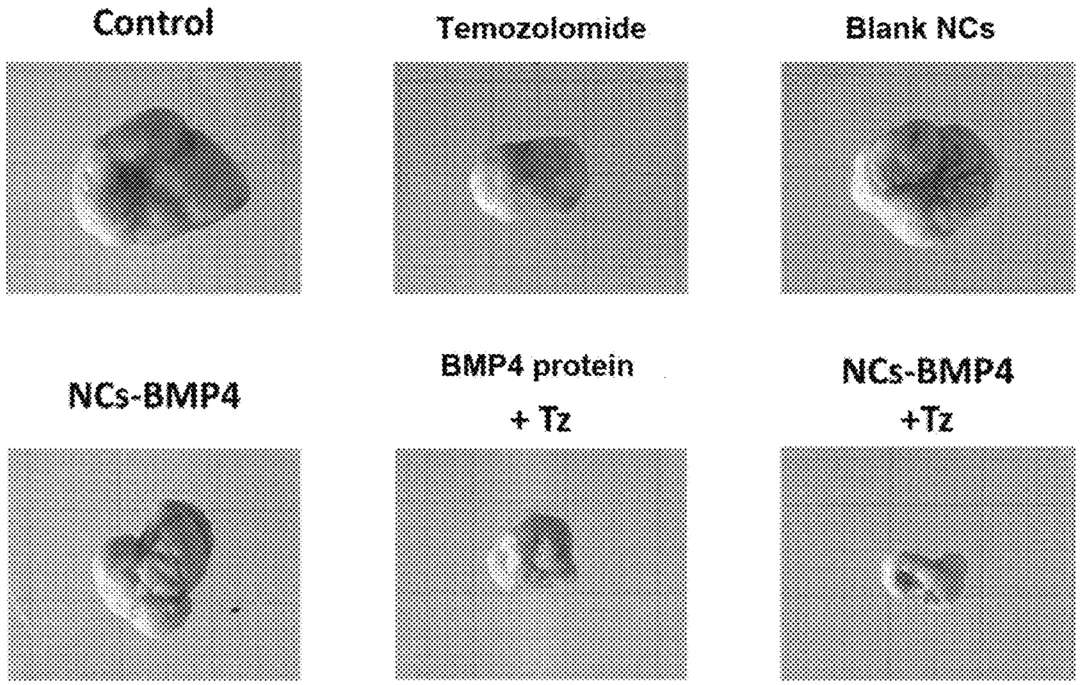
FIG. 6. Photographs of tumors dissected after euthanizing the mice. NCs: Nanocomplexes; BMP4: Bone morphogenetic protein-4; Tz: Temozolomide.

Lastly, an increase in the survival of the animals in the group which combines nanocomplexes-BMP4 with Tz was observed with respect to the control group and to the group treated with Tz alone (FIG. 5*c*). These results were also observed after dissecting the tumors at the end of the assay (FIG. 6).

Figure 7:
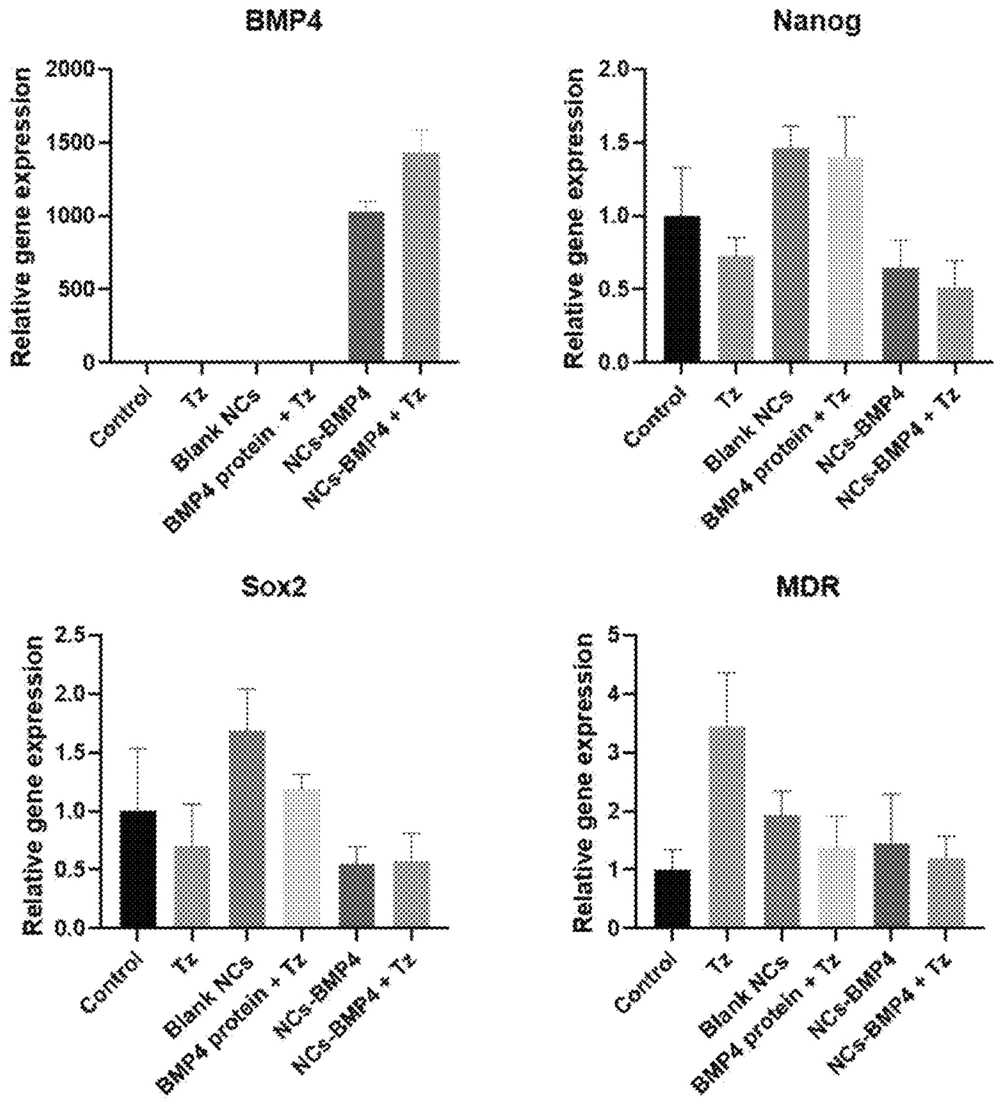
FIG. 7. Representations of the expression of genes involved in tumor development, the expression was analyzed by means of real-time PCR (RT-PCR). NCs: Nanocomplexes; BMP4: Bone morphogenetic protein-4; Tz: Temozolomide.

Finally, the expression of some genes of interest in cancer was analyzed; FIG. 7 shows that after administering the therapeutic nanocomplexes, the expression of BMP4 is more than a thousand times greater with respect to the rest of the groups. The expression of two genes overexpressed in tumor stem cells (Sox2 and Nanog) was also analyzed; in both cases, treatment with the therapeutic nanocomplexes reduced expression, furthermore, an additional effect was observed in Nanog when the nanocomplexes with BMP4 were associated with Tz. Lastly, the expression of a gene involved in resistance to chemotherapeutic agents (MDR) and thereby causing chemotherapy to not be as effective was analyzed after treatment with temozolomide this gene is found to be overexpressed, but association with the nanocomplexes reduces its expression at baseline levels.

The invention claimed is:

1. A polyphosphazene comprising:

at least one hydrocarbon chain (A); and at least one hydrocarbon chain (B) of between 6 and 24 members, wherein between 1 and 4 members are heteroatoms independently selected from O, N and S, and the terminal group of the chain is a group of formula —$NH_2$, wherein the hydrocarbon chain (A) has one of the following structures:

(a)

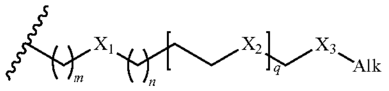

wherein m can have the value 0, 1 or 2, n can have the value 1, 2 or 3, q can have the value 0 or 1, each $X_1$, $X_2$ and $X_3$ are independently selected from the NH, S and O atoms, Alk is a linear or branched $C_1$-$C_6$ alkyl, optionally having a substituent selected from a hydroxyl or thiol group; or (b)

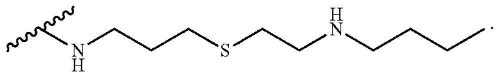

2. The polyphosphazene according to claim 1, wherein the hydrocarbon chains have between 6 and 16 members.

3. The polyphosphazene according to claim 1, wherein 2 or 3 members of the hydrocarbon chains are heteroatoms independently selected from N and S.

4. The polyphosphazene according to claim 1, wherein the hydrocarbon chain (A) is selected from the group consisting of:

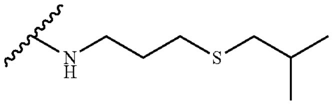

and

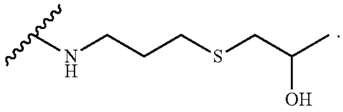

5. A complex comprising a polyphosphazene according to claim 1, and a biologically active molecule.

6. The complex according to claim 5, wherein the biologically active molecule is selected from a protein and a polynucleotide.

7. The complex according to claim 5, wherein the biologically active molecule is a plasmid encoding BMP-4.

8. The complex according to claim 5, further comprising an anionic polyphosphazene.

9. The complex according to claim 8, wherein the anionic polyphosphazene comprises a hydrocarbon chain of between 6 and 24 members, wherein between 1 and 4 members are heteroatoms independently selected from O, N and S, and at least one carboxylic group.

10. The complex according to claim 5, further comprising a chemotherapeutic molecule.

11. The complex according to claim 10, wherein the chemotherapeutic molecule is temozolomide.

12. A pharmaceutical composition comprising the complex according to claim 5, and pharmaceutically acceptable excipients.

13. A method of treating and/or preventing an oncological disease or a disease able to be treated and/or prevented with gene therapy, which method comprises administering to a patient in need of such a treatment a therapeutically effective amount of the pharmaceutical composition according to claim 12.

14. A method of treating and/or preventing brain tumors, which method comprises administering to a patient in need of such a treatment a therapeutically effective amount of the pharmaceutical composition according to claim 12.

15. A method of treating and/or preventing an oncological disease or a disease able to be treated and/or prevented with gene therapy, which method comprises administering to a patient in need of such a treatment a therapeutically effective amount of the complex according to claim 5.

16. A method of treating and/or preventing brain tumors, which method comprises administering to a patient in need of such a treatment a therapeutically effective amount of the complex according to claim 5.

17. The method of claim 16, wherein the brain tumor is a glioblastoma.

18. A kit comprising at least two containers, wherein one of the containers comprises a complex according to claim 5, and the other container comprises a chemotherapeutic molecule, together with instructions for use thereof in the treatment of a disease for sequential or simultaneous administration of both ingredients.

19. A method for the preparation of vectors for transporting biologically active molecules comprising a step of incorporating the complex according to claim 5 as part of said vector.

* * * * *

SEQUENCE LISTING

```
<160> NUMBER OF SEQ ID NOS: 18

<210> SEQ ID NO 1
<211> LENGTH: 22
<212> TYPE: DNA
<213> ORGANISM: Artificial Sequence
<220> FEATURE:
<223> OTHER INFORMATION: GAPDH forward primer

<400> SEQUENCE: 1

gccaaggtca tccatgacaa ct                                              22


<210> SEQ ID NO 2
<211> LENGTH: 21
<212> TYPE: DNA
<213> ORGANISM: Artificial Sequence
<220> FEATURE:
<223> OTHER INFORMATION: GAPDH reverse primer

<400> SEQUENCE: 2

agggccatcc acagtcttct g                                               21


<210> SEQ ID NO 3
<211> LENGTH: 20
<212> TYPE: DNA
<213> ORGANISM: Artificial Sequence
<220> FEATURE:
```

-continued

<223> OTHER INFORMATION: Sox2 forward primer

<400> SEQUENCE: 3
acaccaatcc catccacact 20

<210> SEQ ID NO 4
<211> LENGTH: 20
<212> TYPE: DNA
<213> ORGANISM: Artificial Sequence
<220> FEATURE:
<223> OTHER INFORMATION: Sox2 reverse primer

<400> SEQUENCE: 4
gcaaacttcc tgcaaagctc 20

<210> SEQ ID NO 5
<211> LENGTH: 21
<212> TYPE: DNA
<213> ORGANISM: Artificial Sequence
<220> FEATURE:
<223> OTHER INFORMATION: Nestin forward primer

<400> SEQUENCE: 5
cctcctggag gctgagaact c 21

<210> SEQ ID NO 6
<211> LENGTH: 20
<212> TYPE: DNA
<213> ORGANISM: Artificial Sequence
<220> FEATURE:
<223> OTHER INFORMATION: Nestin reverse primer

<400> SEQUENCE: 6
aaggctggca caggtgtctc 20

<210> SEQ ID NO 7
<211> LENGTH: 21
<212> TYPE: DNA
<213> ORGANISM: Artificial Sequence
<220> FEATURE:
<223> OTHER INFORMATION: Oct4 forward primer

<400> SEQUENCE: 7
cccgccgtat gagttctgtg g 21

<210> SEQ ID NO 8
<211> LENGTH: 22
<212> TYPE: DNA
<213> ORGANISM: Artificial Sequence
<220> FEATURE:
<223> OTHER INFORMATION: Oct4 reverse primer

<400> SEQUENCE: 8
ccgggttttg ctccagcttc tc 22

<210> SEQ ID NO 9
<211> LENGTH: 22
<212> TYPE: DNA
<213> ORGANISM: Artificial Sequence
<220> FEATURE:
<223> OTHER INFORMATION: Nanog forward primer

<400> SEQUENCE: 9
ccgcgccctg cctagaaaag ac 22

-continued

<210> SEQ ID NO 10
<211> LENGTH: 24
<212> TYPE: DNA
<213> ORGANISM: Artificial Sequence
<220> FEATURE:
<223> OTHER INFORMATION: Nanog reverse primer

<400> SEQUENCE: 10
agcctcccaa tcccaaacaa tacg 24

<210> SEQ ID NO 11
<211> LENGTH: 21
<212> TYPE: DNA
<213> ORGANISM: Artificial Sequence
<220> FEATURE:
<223> OTHER INFORMATION: BMP4 forward primer

<400> SEQUENCE: 11
aatgtgacac ggtgggaaac t 21

<210> SEQ ID NO 12
<211> LENGTH: 20
<212> TYPE: DNA
<213> ORGANISM: Artificial Sequence
<220> FEATURE:
<223> OTHER INFORMATION: BMP4 reverse primer

<400> SEQUENCE: 12
cccgctgtga gtgatgctta 20

<210> SEQ ID NO 13
<211> LENGTH: 24
<212> TYPE: DNA
<213> ORGANISM: Artificial Sequence
<220> FEATURE:
<223> OTHER INFORMATION: MDR1 forward primer

<400> SEQUENCE: 13
aacaacgcat tgccatagct cgtg 24

<210> SEQ ID NO 14
<211> LENGTH: 24
<212> TYPE: DNA
<213> ORGANISM: Artificial Sequence
<220> FEATURE:
<223> OTHER INFORMATION: MDR1 reverse primer

<400> SEQUENCE: 14
agtctgcatt ctggatggtg gaca 24

<210> SEQ ID NO 15
<211> LENGTH: 24
<212> TYPE: DNA
<213> ORGANISM: Artificial Sequence
<220> FEATURE:
<223> OTHER INFORMATION: MRP1 forward primer

<400> SEQUENCE: 15
catcgttctg tttgctgccc tgtt 24

<210> SEQ ID NO 16
<211> LENGTH: 24
<212> TYPE: DNA
<213> ORGANISM: Artificial Sequence
<220> FEATURE:
<223> OTHER INFORMATION: MRP1 reverse primer -continued

```
<400> SEQUENCE: 16

agtacgtggt gacctgcaat gagt                                        24


<210> SEQ ID NO 17
<211> LENGTH: 20
<212> TYPE: DNA
<213> ORGANISM: Artificial Sequence
<220> FEATURE:
<223> OTHER INFORMATION: ABCG2 forward primer

<400> SEQUENCE: 17

gccacgtgat tcttccacaa                                             20


<210> SEQ ID NO 18
<211> LENGTH: 20
<212> TYPE: DNA
<213> ORGANISM: Artificial Sequence
<220> FEATURE:
<223> OTHER INFORMATION: ABCG2 reverse primer

<400> SEQUENCE: 18

ttctgcccag gactcaatgc                                             20
```